(12) United States Patent
Schudlo et al.

(10) Patent No.: US 12,014,807 B2
(45) Date of Patent: Jun. 18, 2024

(54) AUTOMATED REPORT GENERATION USING ARTIFICIAL INTELLIGENCE ALGORITHMS

(71) Applicant: Merative US L.P., Ann Arbor, MI (US)

(72) Inventors: Larissa Christina Schudlo, Cambridge, MA (US); Benedikt Graf, Charlestown, MA (US); Marwan Sati, Mississauga (CA)

( * ) Notice: Subject to any disclaimer, the term of this patent is extended or adjusted under 35 U.S.C. 154(b) by 265 days.

(21) Appl. No.: 17/643,743

(22) Filed: Dec. 10, 2021

(65) Prior Publication Data

US 2023/0187039 A1    Jun. 15, 2023

(51) Int. Cl.
*G16H 15/00* (2018.01)
*G16H 40/60* (2018.01)
*G16H 50/20* (2018.01)

(52) U.S. Cl.
CPC ............. *G16H 15/00* (2018.01); *G16H 40/60* (2018.01); *G16H 50/20* (2018.01)

(58) Field of Classification Search
CPC ........ G16H 15/00; G16H 40/60; G16H 50/20; G16H 10/00–80/00
See application file for complete search history.

(56) References Cited

U.S. PATENT DOCUMENTS

| | | | |
|---|---|---|---|
| 8,380,533 B2 | 2/2013 | Reicher | |
| 8,630,970 B2 | 1/2014 | Bryce | |
| 8,712,798 B2 * | 4/2014 | Gotman | A61B 6/563 705/2 |
| 8,824,752 B1 * | 9/2014 | Fonte | A61B 6/481 382/126 |
| 9,569,594 B2 | 2/2017 | Casella Dos Santos | |
| 10,269,449 B2 | 4/2019 | Fram | |
| 10,475,182 B1 * | 11/2019 | Chilamkurhy | G06F 18/2433 |
| 10,499,857 B1 * | 12/2019 | Nguyen | G06N 3/045 |
| 11,210,786 B2 * | 12/2021 | Min | A61B 8/14 |

(Continued)

FOREIGN PATENT DOCUMENTS

| | | |
|---|---|---|
| CN | 104350494 B | 5/2017 |
| EP | 3246836 A1 | 11/2017 |

(Continued)

OTHER PUBLICATIONS

Messina et al., "A Survey on Deep Learning and Explainability for Automatic Image-based Medical Report Generation," arXiv: 2010.10563v1 [cs.CV] Oct. 20, 2020. (Year: 2020).*

(Continued)

*Primary Examiner* — Jonathon A. Szumny
(74) *Attorney, Agent, or Firm* — Stephen J. Walder, Jr.

(57) ABSTRACT

A method, computer system, and a computer program product for automated report generation is provided. The present invention may include receiving a plurality of patient images. The present invention may include retrieving relevant data based on an analysis of the plurality of patient images. The present invention may include providing the relevant data to a user, wherein the relevant data provided to the user is in accordance with a relevant medical guideline. The present invention may include monitoring data input to generate a tailored medical report.

15 Claims, 5 Drawing Sheets

(56) References Cited

U.S. PATENT DOCUMENTS

| | | | | |
|---|---|---|---|---|
| 2004/0181431 | A1* | 9/2004 | Kuth | G16H 15/00 |
| | | | | 705/2 |
| 2005/0096530 | A1* | 5/2005 | Daw | G16H 15/00 |
| | | | | 600/407 |
| 2007/0042869 | A1* | 2/2007 | Pettibon | A63B 23/025 |
| | | | | 482/10 |
| 2008/0120132 | A1* | 5/2008 | Wegenkittl | G16H 30/40 |
| | | | | 705/2 |
| 2008/0126131 | A1* | 5/2008 | Lou | G16H 50/30 |
| | | | | 705/3 |
| 2012/0041779 | A1* | 2/2012 | Boroczky | G16H 40/63 |
| | | | | 705/2 |
| 2013/0083978 | A1* | 4/2013 | Frederick | G16H 30/20 |
| | | | | 382/128 |
| 2013/0191150 | A1* | 7/2013 | Jacob | G16H 10/60 |
| | | | | 705/3 |
| 2013/0218593 | A1* | 8/2013 | Carmeli | G16H 70/60 |
| | | | | 705/3 |
| 2013/0249941 | A1* | 9/2013 | Shao | G06T 11/60 |
| | | | | 345/629 |
| 2013/0326386 | A1* | 12/2013 | Vendrell | G16H 50/30 |
| | | | | 715/771 |
| 2014/0010432 | A1* | 1/2014 | Cohen-Solal | G16H 50/20 |
| | | | | 382/131 |
| 2014/0374476 | A1* | 12/2014 | Ban | G06Q 30/02 |
| | | | | 235/375 |
| 2016/0364526 | A1* | 12/2016 | Reicher | G16H 50/20 |
| 2016/0364862 | A1 | 12/2016 | Reicher | |
| 2017/0337329 | A1* | 11/2017 | Liu | A61B 6/463 |
| 2018/0101645 | A1 | 4/2018 | Sorenson | |
| 2018/0122067 | A1* | 5/2018 | Reicher | A61B 6/463 |
| 2018/0341751 | A1 | 11/2018 | Lyman | |
| 2019/0042703 | A1 | 2/2019 | Reicher | |
| 2019/0198174 | A1* | 6/2019 | Abbaspour | G16H 30/20 |
| 2019/0333218 | A1* | 10/2019 | Bronkalla | G06T 7/0014 |
| 2019/0392944 | A1* | 12/2019 | Samset | G16H 30/40 |
| 2020/0058391 | A1* | 2/2020 | Sevenster | G06V 20/62 |
| 2020/0125598 | A1* | 4/2020 | Trilisky | G06F 16/535 |
| 2020/0273569 | A1* | 8/2020 | Sharma | G16H 50/20 |
| 2020/0303049 | A1* | 9/2020 | Zhang | G06V 10/82 |
| 2020/0364404 | A1* | 11/2020 | Priestas | G06V 30/19173 |
| 2021/0005297 | A1 | 1/2021 | Oez | |
| 2021/0082561 | A1* | 3/2021 | Chang | G16H 40/63 |
| 2021/0118536 | A1 | 4/2021 | Katouzian | |
| 2021/0166807 | A1* | 6/2021 | Quennesson | G06N 20/00 |
| 2021/0334968 | A1* | 10/2021 | Peng | G06T 7/10 |
| 2021/0407694 | A1* | 12/2021 | Deckert | G16H 15/00 |
| 2022/0037019 | A1* | 2/2022 | Covington | G06T 7/0012 |
| 2022/0293271 | A1* | 9/2022 | Chang | G16H 15/00 |
| 2023/0154596 | A1* | 5/2023 | Moustafa | G16H 50/70 |
| | | | | 705/2 |

FOREIGN PATENT DOCUMENTS

| | | | |
|---|---|---|---|
| EP | 3696818 | A1 * | 8/2020 |
| KR | 20190071724 | A | 6/2019 |
| RU | 2620890 | C2 | 5/2017 |

OTHER PUBLICATIONS

Zhang et al., "Automated Radiological Report Generation For Chest X-Rays With Weakly-Supervised End-to-End Deep Learning," arXiv:2006.10347v1 [cs.CV] Jun. 18, 2020. (Year: 2020).*

Yin et al., "Automatic Generation of Medical Imaging Diagnostic Report with Hierarchical Recurrent Neural Network," 2019 IEEE International Conference on Data Mining (ICDM); DOI 10.1109/ICDM.2019.00083. (Year: 2019).*

Alfarghaly, et al., "Automated Radiology Report Generation using Conditioned Transformers," Informatics in Medicine Unlocked, Mar. 2021, vol. 24, 8 pages, ScienceDirect, Retrieved from the Internet: <URL: https://www.sciencedirect.com/science/article/pii/S2352914821000472>.

Carstens, "Automatic Linkage and Synchronized Annotation in Radiology." IP.com, Mar. 27, 2009, 2 pages, IP.com No. IPCOM000180632D, Siemens AG, Retrieved from the Internet: <URL: https://priorart.ip.com/IPCOM/000180632>.

Huang, et al., "Multi-Attention and Incorporating Background Information Model for Chest X-Ray Image Report Generation," IEEE Access, Oct. 14, 2019, pp. 154808-154817, DOI: 10.1109/ACCESS.2019.2947134, IEEE, Retrieved from the Internet: <URL: https://ieeexplore.ieee.org/document/8867873>.

Kisilev, et al., "From medical image to automatic medical report generation," IBM Journal of Research and Development, Apr. 24, 2015, pp. 2:1-2:7, vol. 59, Issue: 2/3, DOI: 10.1147/JRD.2015.2393193, IBM, Retrieved from the Internet: <URL: https://ieeexplore.ieee.org/document/7094968?reload=true>.

Liu, et al, "Exploring and Distilling Posterior and Prior Knowledge for Radiology Report Generation," ArXiv [journal], Jun. 26, 2021, 10 pages, arXiv:2106.06963v2, Retrieved from the Internet: <URL: https://www.semanticscholar.org/paper/Exploring-and-Distilling-Posterior-and-Prior-for-Liu-Wu/279925dbe2ebe4e38d6cfa646f726aa8d6d9a122>.

Mell, et al., "The NIST Definition of Cloud Computing", National Institute of Standards and Technology, Special Publication 800-145, Sep. 2011, 7 pages.

Xie, et al., "A Survey on Incorporating Domain Knowledge into Deep Learning for Medical Image Analysis," Feb. 8, 2021, 27 pages, arXiv:2004.12150v4, Cornell University, Retrieved from the Internet: <URL: https://arxiv.org/abs/2004.12150>.

Yang, et al., "Automatic Ultrasound Image Report Generation With Adaptive Multimodal Attention Mechanism," Neurocomputing [abstract only], Feb. 2021, pp. 40-49, vol. 427, Retrieved from the Internet: <URL: https://www.sciencedirect.com/science/article/abs/pii/S0925231220316660?via%3Dihubol>.

Yuan, et al., "Automatic Radiology Report Generation Based on Multi-view Image Fusion and Medical Concept Enrichment," Futrewei Technologies, Inc., Jul. 23, 2019, 9 pages, Retrieved from the Internet: <URL: https://arxiv.org/abs/1907.09085>.

Zhang, et al., "When Radiology Report Generation Meets Knowledge Graph," The Thirty-Fourth AAAI Conference on Artificial Intelligence (AAAI-20), 2020, pp. 12910-12917.

* cited by examiner

AUTOMATED REPORT GENERATION USING ARTIFICIAL INTELLIGENCE ALGORITHMS

BACKGROUND

The present invention relates generally to the field of computing, and more particularly to automated report generation.

When generating a medical report, such as, but not limited to, a radiology report, it may be necessary for a clinician to at least, link imaging observations to specific medical guidelines, extract specific measurements from current imaging, and/or identify relevant data from a patient's medical record, in order to make a complete diagnosis. Unstructured medical reports may be free-form documents and may not have specific reporting requirements in accordance with medical guidelines.

Accordingly, clinicians may often be forced to recall medical standards from memory and/or manually retrieve specific medical guidelines in order to generate a complete medical report in accordance with the specific medical guidelines.

SUMMARY

Embodiments of the present invention disclose a method, computer system, and a computer program product for automated report generating. The present invention may include receiving a plurality of patient images. The present invention may include retrieving relevant data based on an analysis of the plurality of patient images. The present invention may include providing the relevant data to a user, wherein the relevant data provided to the user is in accordance with a relevant medical guideline. The present invention may include monitoring data input to generate a tailored medical report.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for *medica*; report generating. As such, the present embodiment has the capacity to improve the technical field of automated report generation by retrieving medical guidelines and/or relevant patient data based on a plurality of patient images and monitoring medical report generation. More specifically, the present invention may include receiving a plurality of patient images. The present invention may include retrieving relevant data based on an analysis of the plurality of patient images. The present invention may include providing the relevant data to a user, wherein the relevant data provided to the user is in accordance with a relevant medical guideline. The present invention may include monitoring data input to generate a tailored medical report.

As described previously, when generating a medical report, such as, but not limited to a radiology report, it may be necessary for a clinician to at least, link imaging observations to specific medical guidelines, extract specific measurements from current imaging, or identify relevant data from a patient's medical record, in order to make a complete diagnosis. Unstructured medical reports may be free-form documents and may not have specific reporting requirements in accordance with medical guidelines.

Accordingly, clinicians may often be forced to recall medical standards from memory and/or manually retrieve specific medical guidelines in order to generate a complete medical report in accordance with the specific medical guidelines.

Therefore, it may be advantageous to, among other things, receive a plurality of patient images, retrieve relevant data based on an analysis of the plurality of patient images, provide relevant data to a user, wherein the relevant data provided to the user is in accordance with relevant medical guidelines, and monitor data input for a medical report.

According to at least one embodiment, the present invention may improve diagnosis and/or medical report generation by utilizing at least imaging machine learning models and/or text-monitoring machine learning models in generating contextual information for identifying and/or summarizing, patient-specific information which may be displayed to a user.

According to at least one embodiment, the present invention may improve diagnosis and/or medical report generation by applying imaging and/or text-monitoring machine learning models in deriving insights and presenting key information from a plurality of data sources to the user. The plurality of data sources may include, but are not limited to including, medical standards and/or guidelines, relevant data extracted from a patient's medical record, and/or information/measurements from current imaging.

According to at least one embodiment, the present invention may improve medical report generation by providing relevant data to the user, monitoring input for the medical report, providing one or more recommendations, and/or pre-populating the medical report based on data analysis of the plurality of patient images.

According to at least one embodiment, the present invention may improve adherence with standard medical guidelines by utilizing insights from both imaging and text algorithms in identifying the relevant guidelines for a given patient and then automatically retrieving information from current imaging and/or a patient's medical record to populate a medical report, provide follow-up suggestions, and highlight or identify missing information for a clinician.

Figure 1:
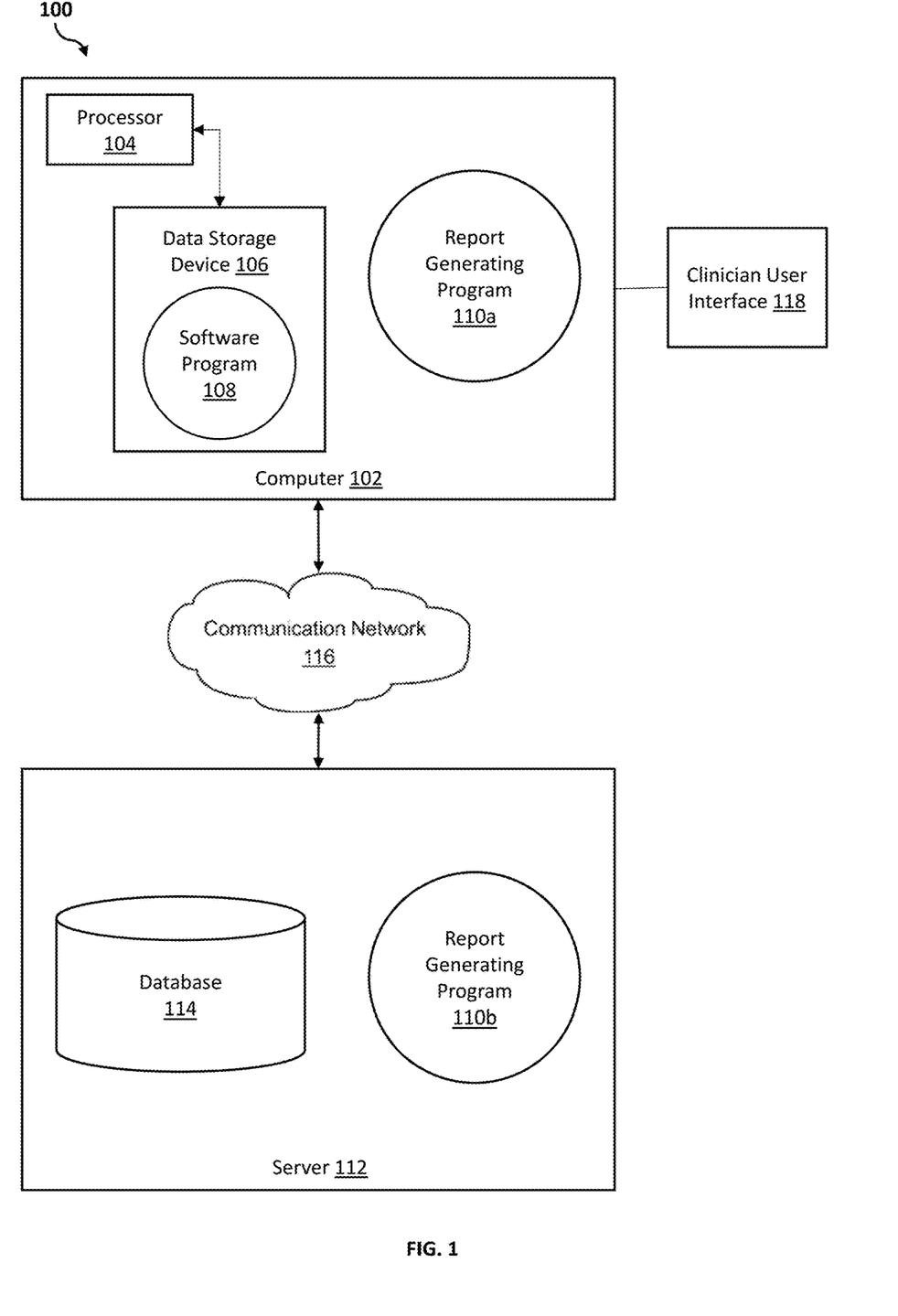
FIG. 1 illustrates a networked computer environment according to at least one embodiment.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and a report generating program 110a. The networked computer environment 100 may also include a server 112 that is enabled to run a report generating program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 3, server computer 112 may include internal components 902a and external components 904a, respectively, and client computer 102 may include internal components 902b and external components 904b, respectively. Server computer 112 may also operate in a cloud computing service model, such as Software as a Service (SaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the report generating program 110a, 110b may interact with a database 114 that may be embedded in various storage devices, such as, but not limited to a computer/mobile device 102, a networked server 112, or a cloud storage service.

According to the present embodiment, a user using a client computer 102 or a server computer 112 may use the report generating program 110a, 110b (respectively) to generate medical reports in accordance with medical guidelines. The report generating method is explained in more detail below with respect to FIG. 2.

Figure 2:
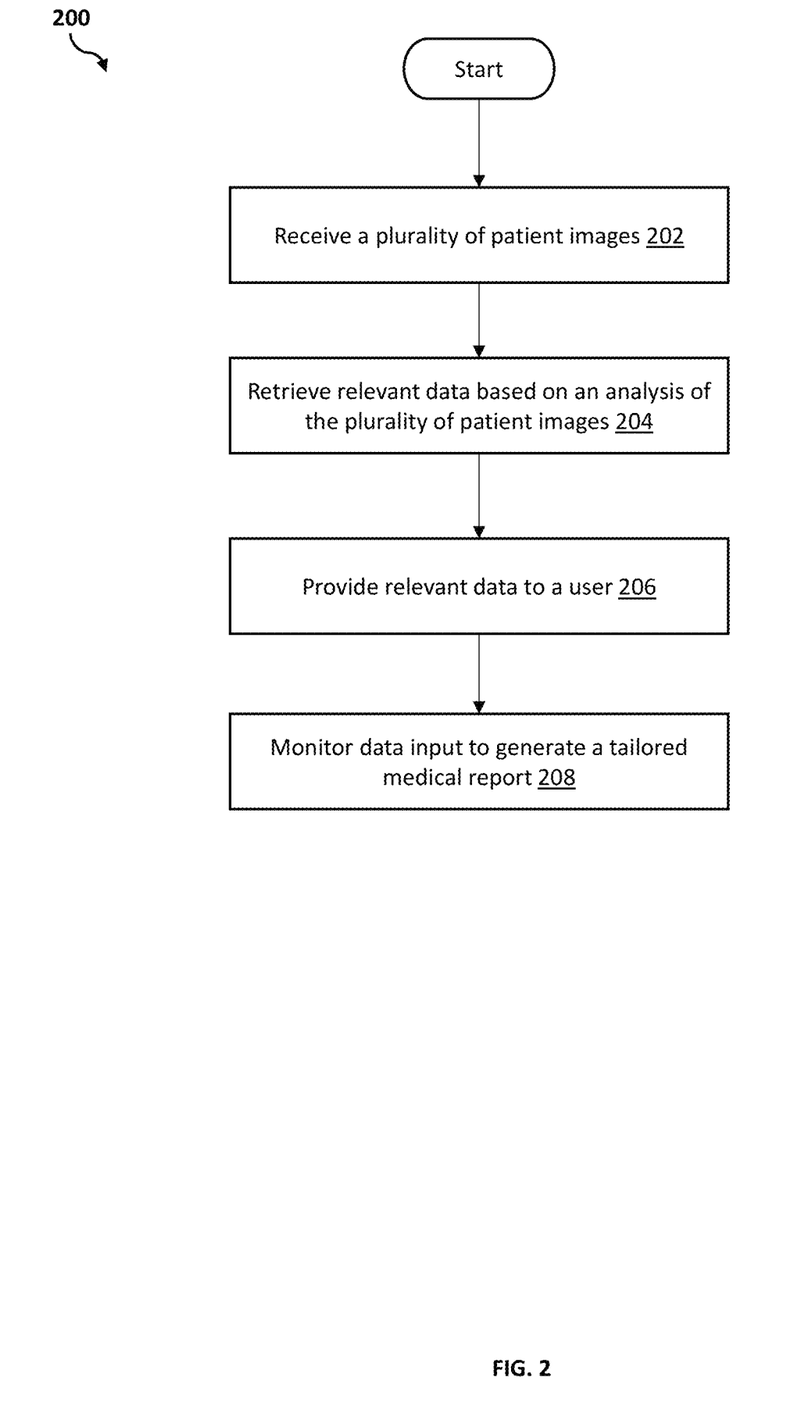
FIG. 2 is an operational flowchart illustrating a process for medical report generation according to at least one embodiment.

Referring now to FIG. 2, an operational flowchart illustrating the exemplary report generating process 200 used by the report generating program 110a and 110b according to at least one embodiment is depicted.

At 202, the report generating program 110 receives a plurality of patient images. The report generating program 110 may receive the plurality of patient images in real time from a connected database (e.g., database 114). The connected database (e.g., database 114) may receive the plurality of images from one or more modalities (e.g., source machine types), such as, but not limited to, X-ray machines, computer axial tomography (CAT) machines, and/or magnetic resonance imaging (MRI) machines, amongst other machines currently utilized in radiology and/or hereinafter developed.

The connected database (e.g., database 114) may, for example, be a Picture Archiving and Communication System ("PACS") database, the PACS database may utilize medical imaging technology which may provide economical storage and/or real time access to images sourced from one or more modalities (e.g., source machine types). The format utilized by PACS image storage and/or access may be a standard format for images utilized by a physician and/or radiologist, such as, but not limited to Digital Imaging and Communications in Medicine ("DICOM"). DICOM may be the standard format for medical images, DICOM files may include, but are not limited to including, a plurality of patient images and corresponding details with respect to the patient. The DICOM files may be accessed and/or viewed by the physician and/or radiologist through the report generating program 110 in a clinician user interface 118.

The report generating program 110 may utilize one or more imaging machine learning models in analyzing the plurality of patient images. The imaging machine learning models may be pretrained utilizing one or more publicly available datasets and/or the PACS database maintained by the report generating program 110. The imaging machine learning models may include, but are not limited to including, two-dimensional and/or three-dimensional deep learning convolutional neural network (CNN) models for at least classification and/or segmentation. For example, the report generating program 110 may utilize CNN classification models such as, but not limited to, Deep Residual Networks (ResNet), Dense Convolutional Networks (DenseNet), and/or EfficientNet, amongst other CNN classification models. The report generating program 110 may also utilize CNN segmentation models, such as, but not limited to, U-Net and/or Dense U-Net, amongst other CNN segmentation models.

At 204, the report generating program 110 retrieves relevant data based on the analysis of the patient images. The report generating program 110 may retrieve relevant data based on each positive finding within the patient images identified using the imaging machine learning models. The report generating program 110 may retrieve relevant data, such as, but not limited to, relevant medical guidelines and/or patient data. The report generating program 110 may retrieve the relevant data utilizing at least one or more text-monitoring machine learning models. As will be explained in more detail below with respect to step 208 the text-monitoring machine learning models may also be utilized by the report generating program 110 in monitoring input for a medical report.

The one or more text-monitoring machine learning models utilized by the report generating program 110 may include, but are not limited to including, rule-based algorithms and/or deep-learning natural language processing (NLP) models, such as, but not limited to, Long-Short Term Memory (LSTM) networks and/or Bidirectional Encoder Representations from Transformers (BERT). For example, the report generating program 110 may identify one or more lung nodules within the plurality of patient images utilizing the imaging machine learning models and/or one or more object detection models, such as, but not limited to Fast-R CNN. The report generating program 110 may determine characteristics of the one or more lung nodules, such as, but not limited to, size, density, and/or location of the lung nodules utilizing the one or more CNN segmentation models. The report generating program 110 may leverage this information in retrieving the relevant medical guidelines and/or patient data utilizing at least the text-monitoring algorithms. In another embodiment, the retrieval may be done utilizing a database look-up for each positive finding supported by the imaging machine learning models based on at least, keywords and/or patient parameters.

The relevant medical guidelines retrieved by the report generating program 110 may depend on the analysis of the plurality of images performed utilizing the imaging machine learning methods. The report generating program 110 may retrieve the relevant medical guidelines based on the type of patient images, patient data, geographic location, and/or the analysis of the images. For example, the report generating program 110 may retrieve the Fleischner criteria (e.g., Fleischner Society Guidelines) for pulmonary nodule detection, American College of Radiology® (ACR® and all ACR-based trademarks are trademarks or registered trademarks of The American College of Radiology Corporation in the United States and/or other countries) guidelines for Mediastinal and Cardiovascular Incidental Findings for aortic aneurysm detection, and American College of Gastroenterology (ACG) guidelines for diagnosis and management of pancreatic cysts for pancreatic cyst detection. In the above examples, the report generating program 110 may retrieve patient data in accordance with the relevant medical guidelines and only after receiving patient consent. For example, for the Fleischner criteria (e.g., Fleischner Society Guidelines), the report generating program 110 may retrieve patient data such as, but not limited to, age and/or other lung cancer risk factors. For the ACR® guidelines or Mediastinal and Cardiovascular Incidental Findings for aneurysm detection the report generating program 110 may retrieve patient data related to history of pancreatitis. For the ACG guidelines for diagnosis and management of pancreatic cysts for pancreatic cyst detection the report generating program 110 may retrieve patient data related to a history of connective tissue diseases, such as, but not limited to, Marfan and/or Ehlers-Danlos disease.

All patient data accessed and/or received by the report generating program 110 including, but not limited to including, Electronic Health Records (EHRs), the plurality of patient images and/or other imaging from medical records, amongst other patient data shall not be construed as to violate and/or encourage the violation of any local, state, federal, or international law with respect to data privacy protection. The report generating program 110 may require consent by the patient and/or user on behalf of the patient prior to receiving and/or accessing any patient data. The report generating program 110 may intermittently confirm with the patient and/or the user whether the report generating program 110 may be granted continued access to the patient data. As will be explained in more detail below, the report generating program 110 may utilize patient data in identifying similar patients based on the plurality of patient images received. The report generating program 110 may only maintain patient data within the connected database (e.g., database 114) in which the report generating program 110 received consent.

The report generating program 110 may only retrieve patient data which may be necessary for patient care and/or follow-up suggestions. Continuing with the above example, the report generating program 110 may access only patient data relevant to the lung nodules positively identified. In this example, the report generating program 110 may access patient data, such as, but not limited to, patient demographic information, previous reporting of lung nodules, patient risk data, amongst other relevant patient data.

In an embodiment, the report generating program 110 may also determine a score based on the plurality of patient images. The score may be based on the relevant medical guidelines and utilized in describing the patient images. For example, in radiology Reporting and Data Systems (RADS) scores may be utilized in describing imaging results. Examples of RADS scores may include, but are not limited to including, BI-RADS® (Breast Imaging Reporting and Data System) scores, PI-RADS® (Prostate Imaging Reporting and Data System) scores, LI-RADS® (Liver Reporting and Data System) scores, TI-RADS® (Thyroid Imaging Reporting and Data System) scores, O-RADS® (Ovarian-Adnexal Reporting and Data System) scores, NI-RADS™ (Head and Neck Reporting and Data System) scores, Lung-RADS® (Lung Reporting and Data System) scores, HI-RADS™ (Head Injury Reporting and Data System) scores, CAD-RADS™ (Coronary Artery Disease Reporting and Data System) scores, C-GRADS™ (CT Colonography Reporting and Data System) scores, and/or other RADS scores (All RADS trademarks and/or RADS-based trademarks are trademarks or registered trademarks of The American College of Radiology Corporation in the United States and/or other countries). As will be explained in more detail below the RADS scores may be at least part of the relevant data provided to the user by the report generating program 110.

At 206, the report generating program 110 provides relevant data to a user. The relevant data provided to the user may include, but is not limited to including, relevant medical guidelines, imaging measurements and/or information, relevant patient data, logic and/or calculations such as RADS scores, one or more recommendations, missing data, amongst other relevant data. The report generating program 110 may provide the relevant data to the user in the clinician user interface 118.

In an embodiment, the report generating program 110 may generate a checklist of items in accordance with the relevant medical guidelines in which the user may reference in generating a medical report. The checklist of items may be displayed by the report generating program 110 in the clinician user interface 118.

In an embodiment, the report generating program 110 may provide the relevant data to the user by pre-populating a medical report. The report generating program 110 may pre-populate the medical report in accordance with the relevant medical guidelines retrieved in step 204.

The report generating program 110 may also provide the user with one or more recommendations, such as, but not limited to, follow-up recommendations, missing information (e.g., requiring user input), recommended timelines for follow-up appointments, treatment recommendations, amongst other recommendations. For example, the text monitoring machine learning models may analyze the patient's medical record for mention of a finding made in the current study based on the plurality of patient images. The report generating program 110 may notify the user whether or not the previous finding was acted upon and/or raise alerts for previously detected conditions that may require a follow up, such as a 6-month mammography and/or lung exam follow up.

The report generating program 110 may provide the one or more recommendations based on similar patients identified through at least the connected database (e.g., database 114), publicly available databases and/or studies, and/or databases associated with the user. The report generating program 110 may utilize the similar patients identified and/or similar patient case histories in recommending treatments, further imaging, and/or identifying additional information which may be included in the medical report. The report generating program 110 may only identify similar patients in which the report generating program 110 received consent from the similar patient and/or on behalf of the similar patient and may only access similar patient data required in the treatment of the patient for which the plurality of patient images may be received. The report generating program 110 may utilize information retrieval algorithms, such as, but not limited to, Latent Semantic Indexing, in identifying similar patient records within the connected database (e.g., database 114). the publicly available databases and/or studies, and/or databases associated with the user.

At 208, the report generating program 110 monitors data input to generate a tailored medical report. The data input may be entered by the user based on the relevant data provided to the user by the report generating program 110. The report generating program 110 may monitor data input to generate the tailored medical report using at least the one or more text-monitoring machine learning models described in step 204.

The report generating program 110 may also monitor the user using click actions. Click actions may include, but are not limited to including, cursor tracking, tool utilization, locating prior studies for a patient which may be relevant for the medical report currently being generated, clicking through the plurality of patient images, scrolling through a patient's medical history, enabling a dictation feature, report interaction, and/or generating a report, amongst other click actions which may be utilized by the report generating program 110 in monitoring the user. For example, if the user types "the prior image" the report generating program 110 using the text-monitoring machine learning models may detect the user input in real time and automatically retrieve and display the prior image from the plurality of patient images in the clinician user interface 118.

In an embodiment, the report generating program 110 may complete measures and/or observations based on the click actions of the user. For example, the user may click a nodule within one of the patient images and the imaging machine learning models may determine the relevant information, such as, size and/or location. In this example the report generating program 110 may automatically populate the medical report based on the click action of the user with "Nodule size 6 millimeters in the left lung." The report generating program 110 may further utilize the segmentation models, such as U-Net, and object detection models, such as Fast RCNN, to identify the organ and/or object the user is interacting with based on the click actions of the user.

The report generating program 110 may utilize at least the imaging machine learning models and/or text-monitoring machine learning models to embed one or more PACS links within the tailored medical report. For example, if the medical report being generated includes a reference to a specific image, anatomic location, and/or finding, the report generating program 110 may automatically identify this location in the plurality of patient images and embed the PACS link within the medical report being generated for the region on interest.

In an embodiment, the report generating program 110 may generate the tailored medical report in which the report generating program 110 may monitor the data input by the user. The tailored medical report generated by the report generating program 110 may be pre-populated with the relevant data provided to the user at step 206 in accordance with the relevant medical guidelines retrieved in step 204. The tailored medical report generated by the report generating program 110 may be displayed to the user in the clinician user interface. The clinician may edit and/or provide data input to the medical report in the clinician user interface 118. The edits and/or data provided by the user being monitored by the report generating program 110 utilizing at least the machine learning models described above. The report generating program 110 may utilize one or more visual indicators within the tailored medical report generated in displaying the one or more recommendations to the user and/or identifying additional information which may be required in the medical report based on a relevant medical guideline.

The report generating program 110 may include details and/or instructions for the user on gathering the additional information which may be required in the tailored medical report based on the relevant medical guidelines. For example, the report generating program 110 may determine additional patient images may be required in completing the medical report in accordance with a relevant medical guideline. The report generating program 110 may suggest one or more modalities (e.g., source machine types) which may be utilized, regions requiring further imaging, amongst other instructions. The instructions may be embedded within the medical report such that the user may utilize a click action to retrieve the instructions. For example, a red colored flag may be utilized as an indicator within the medical report for additional information which may be required. The red colored flag being adjacent to corresponding blank field within the medical report. The user may hover the cursor over the red colored flag at which time the report generating program 110 may display the recommended instructions to the user for completing the additional information required in the medical report based on the relevant medical guideline.

It may be appreciated that FIG. 2 provides only an illustration of one embodiment and do not imply any limitations with regard to how different embodiments may be implemented. Many modifications to the depicted embodiment(s) may be made based on design and implementation requirements.

Figure 3:
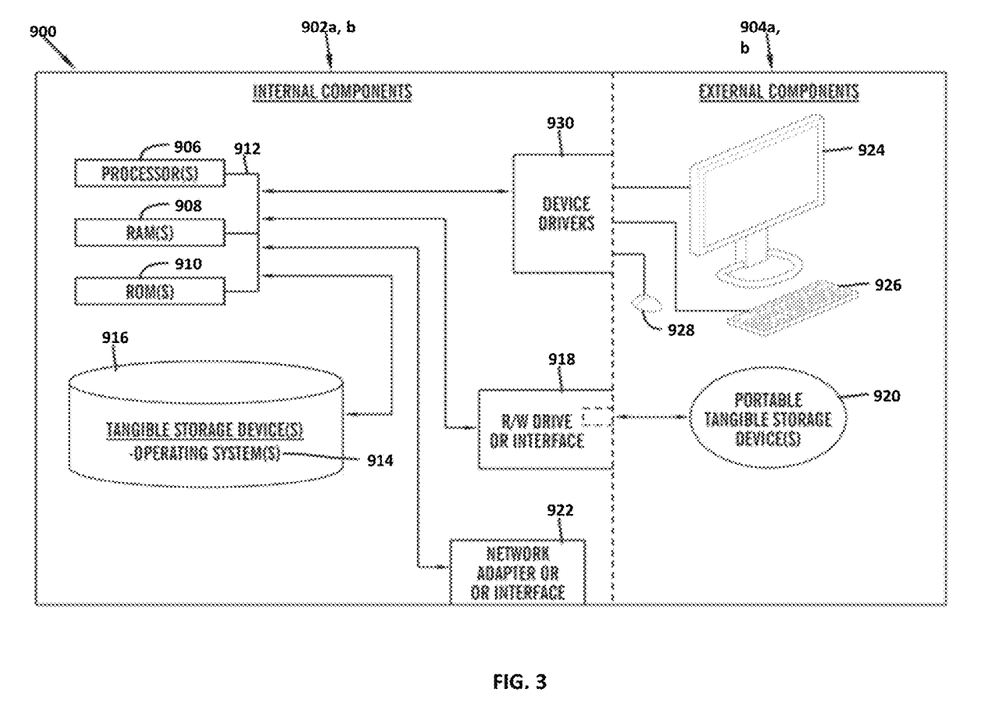
FIG. 3 is a block diagram of internal and external components of computers and servers depicted in FIG. 1 according to at least one embodiment.

FIG. 3 is a block diagram 900 of internal and external components of computers depicted in FIG. 1 in accordance with an illustrative embodiment of the present invention. It should be appreciated that FIG. 3 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902a, b and external components 904a, b illustrated in FIG. 3. Each of the sets of internal components 902a, b includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108, and the report generating program 110a in client computer 102, and the report generating program 110b in network server 112, may be stored on one or more computer-readable tangible storage devices 916 for execution by one or more processors 906 via one or more RAMs 908 (which typically include cache memory). In the embodiment illustrated in FIG. 3, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902a, b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the report generating program 110a and 110b can be stored on one or more of the respective portable computer-readable tangible storage devices 920, read via the respective R/W drive or interface 918 and loaded into the respective hard drive 916.

Each set of internal components 902a, b may also include network adapters (or switch port cards) or interfaces 922 such as a TCP/IP adapter cards, wireless wi-fi interface cards, or 3G or 4G wireless interface cards or other wired or wireless communication links. The software program 108 and the report generating program 110a in client computer 102 and the report generating program 110b in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the report generating program 110a in client computer 102 and the report generating program 110b in network server computer 112 are loaded into the respective hard drive 916. The network may comprise copper wires, optical fibers, wireless transmission, routers, firewalls, switches, gateway computers and/or edge servers.

Each of the sets of external components 904a, b can include a computer display monitor 924, a keyboard 926, and a computer mouse 928. External components 904a, b can also include touch screens, virtual keyboards, touch pads, pointing devices, and other human interface devices. Each of the sets of internal components 902a, b also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
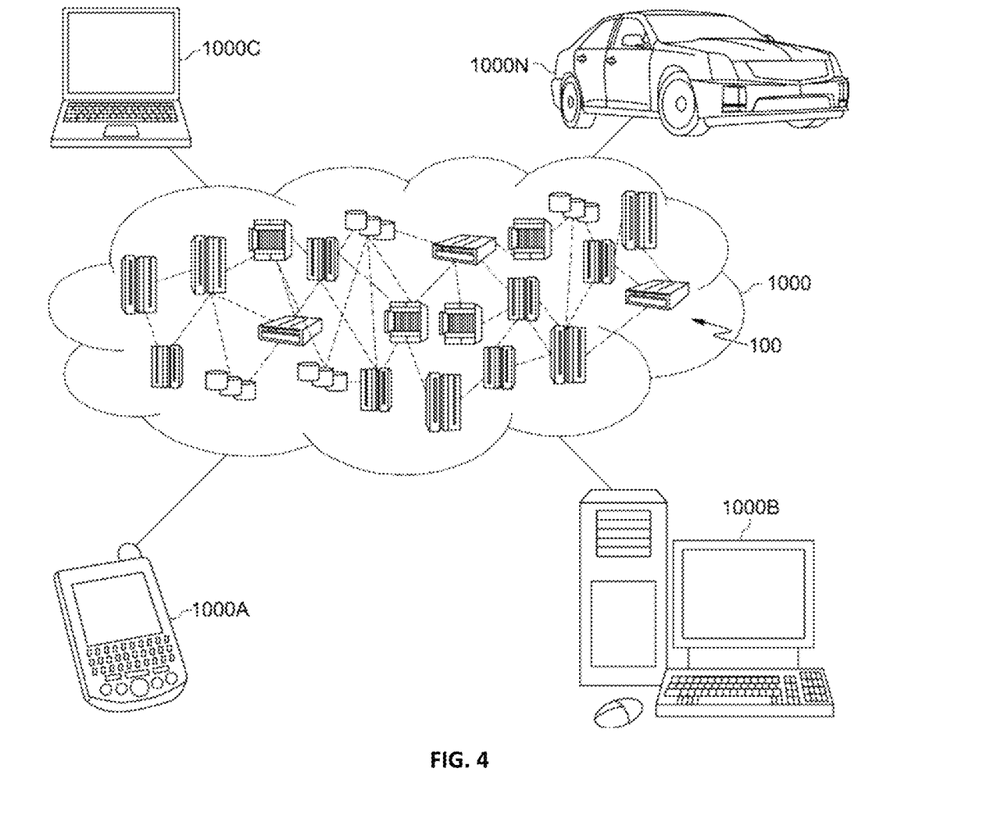
FIG. 4 is a block diagram of an illustrative cloud computing environment including the computer system depicted in FIG. 1, in accordance with an embodiment of the present disclosure.

Referring now to FIG. 4, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 4 are intended to be illustrative only and that computing nodes 100 and cloud computing environment 1000 can communicate with any type of computerized device over any type of network and/or network addressable connection (e.g., using a web browser).

Figure 5:
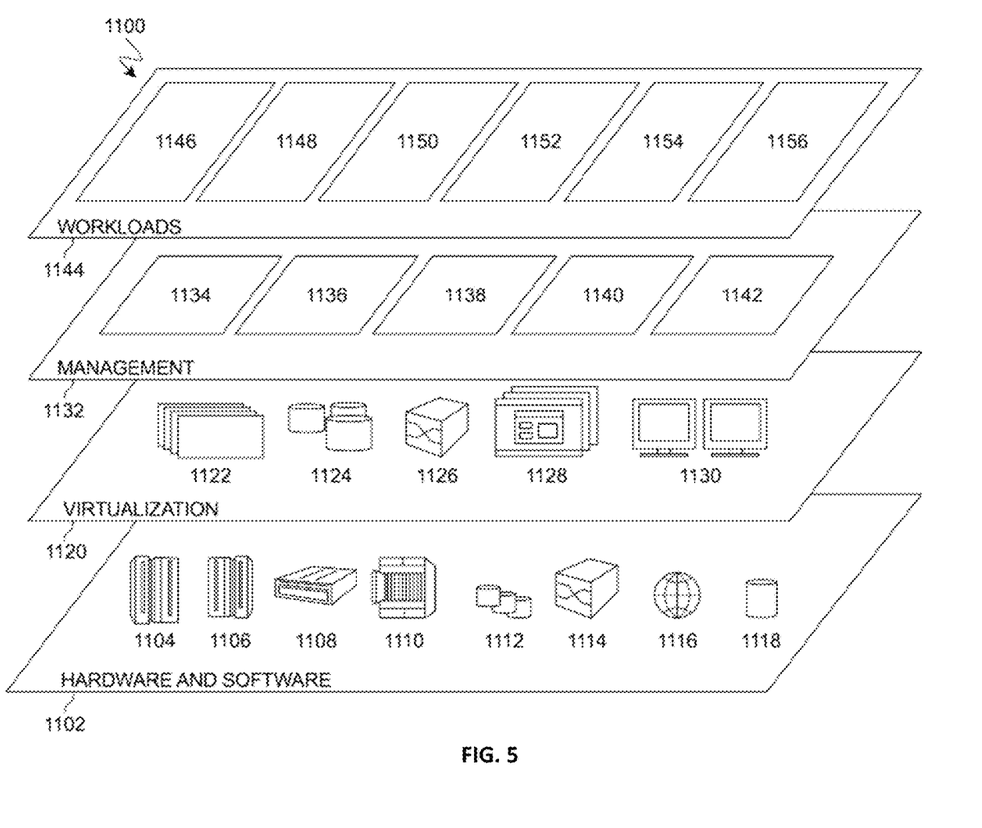
FIG. 5 is a block diagram of functional layers of the illustrative cloud computing environment of FIG. 4, in accordance with an embodiment of the present disclosure.

Referring now to FIG. 5, a set of functional abstraction layers 1100 provided by cloud computing environment 1000 is shown. It should be understood in advance that the components, layers, and functions shown in FIG. 5 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and report generating program 1156. A report generating program 110a, 110b provides a way to generate medical reports in accordance with relevant medical guidelines.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

The present disclosure shall not be construed as to violate or encourage the violation of any local, state, federal, or international law with respect to privacy protection.

What is claimed is:

1. A method, executed within a data processing system comprising at least one processor and at least one memory, the at least one memory comprising instructions executed by the at least one processor to specifically configure the data processing system to implement a medical report generation computer system that performs the method, the method comprising:

receiving, by the medical report generation computer system, a plurality of patient images of a patient;

executing, in the medical report generation computer system, an imaging machine learning model on the plurality of patient images to output, based on a processing of the plurality of patient images through the imaging machine learning model, a medical image positive finding, wherein the imaging machine learning model is a convolutional neural network (CNN) pre-trained based on a database of existing patient medical images;

executing, in the medical report generation computer system, a segmentation CNN model on the plurality of patient images to identify characteristics of the medical image positive finding;

executing, in the medical report generation computer system, a text monitoring machine learning model based on the medical image positive finding and the characteristics of the medical image positive finding, to retrieve relevant data comprising relevant patient data, from a patient medical record of the patient, and a relevant medical guideline corresponding to the medical image positive finding and the characteristics of the medical image positive finding, wherein different relevant medical guidelines and patient data are retrieved for different medical image positive findings and different characteristics of the medical image positive finding;

providing the relevant data to a user, wherein the relevant data provided to the user is in accordance with the relevant medical guideline; and monitoring data input to generate a tailored medical report, wherein the text monitoring machine learning model searches for a previous mention in the patient medical record of a previous finding corresponding to the medical image positive finding, wherein providing the relevant data to the user comprises providing an output that specifies whether the previous finding was acted upon and raises an alert for previously detected conditions that require a follow up, and wherein monitoring data input to generate the tailored medical report comprises:

monitoring a user click action on at least one patient image in the plurality of patient images; and modifying an output of the relevant data to the user based on the user click action to provide relevant information corresponding to a portion of the at least one patient image clicked on by the user click action.

2. The method of claim 1, wherein the medical image positive finding is one of a pulmonary nodule, an aortic aneurysm, or a pancreatic cyst, and wherein a different relevant medical guideline is retrieved depending on which medical image positive finding is identified in the plurality of patient images.

3. The method of claim 1, wherein the relevant medical guideline is retrieved based on a type of the plurality of the patient images, the relevant patient data, and a geographic location.

4. The method of claim 1, wherein providing the relevant data to the user comprises presenting information gathering guidelines for gathering additional patient images based on the relevant medical guideline in order to complete the tailored medical report, wherein the information gathering guidelines comprise a recommended modality for the additional patient images and regions requiring further imaging.

5. The method of claim 1, wherein monitoring data input to generate the tailored medical report comprises embedding, in the output, one or more links to one or more patient images comprising the medical image positive finding.

6. The method of claim 1, wherein the characteristics comprise at least a size and a location of the medical image positive finding.

7. The method of claim 1, further comprising:

providing one or more recommendations to the user, wherein the one or more recommendations are based on at least one or more similar patients identified in a connected database, wherein the one or more similar patients are identified in the connected database using at least one information retrieval algorithm.

8. The method of claim 1, wherein modifying the output based on the user click action comprises automatically populating the tailored medical report based on the user click action with information about the portion of the at least one patient image clicked on by the user click action.

9. The method of claim 1, wherein modifying the output based on the user click action comprises executing the segmentation CNN model on the portion of the at least one patient image clicked on by the user click action to identify an organ or object clicked on by the user click action.

10. The method of claim 1, wherein monitoring data input to generate the tailored medical report comprises monitoring, in real time by the text monitoring machine learning model, text entered by the user into an interface and modifying an output of the relevant data to the user in real time based on an analysis of the text entered by the user into the interface.

11. A computer system for medical report generation, comprising:

one or more processors, one or more computer-readable memories, one or more computer-readable tangible storage medium, and program instructions stored on at least one of the one or more tangible storage medium for execution by at least one of the one or more processors via at least one of the one or more memories to specifically configure the computer system to implement a medical report generation computer system, wherein the medical report generation computer system operates to perform a method comprising:

receiving, by the medical report generation computer system, a plurality of patient images of a patient;

executing, in the medical report generation computer system, an imaging machine learning model on the plurality of patient images to output, based on a processing of the plurality of patient images through the imaging machine learning model, a medical image positive finding, wherein the imaging machine learning model is a convolutional neural network (CNN) pretrained based on a database of existing patient medical images;

executing, in the medical report generation computer system, a segmentation CNN model on the plurality of patient images to identify characteristics of the medical image positive finding;

executing, in the medical report generation computer system, a text monitoring machine learning model based on the medical image positive finding and the characteristics of the medical image positive finding, to retrieve relevant data comprising relevant patient data, from a patient medical record of the patient, and a relevant medical guideline corresponding to the medical image positive finding and the characteristics of the medical image positive finding, wherein different relevant medical guidelines and patient data are retrieved for different medical image positive findings and different characteristics of the medical image positive finding;

providing the relevant data to a user, wherein the relevant data provided to the user is in accordance with the relevant medical guideline; and monitoring data input to generate a tailored medical report, wherein the text monitoring machine learning model searches for a previous mention in the patient medical record of a previous finding corresponding to the medical image positive finding, wherein providing the relevant data to the user comprises providing an output that specifies whether the previous finding was acted upon and raises an alert for previously detected conditions that require a follow up, and wherein monitoring data input to generate the tailored medical report comprises:

monitoring a user click action on at least one patient image in the plurality of patient images; and modifying an output of the relevant data to the user based on the user click action to provide relevant information corresponding to a portion of the at least one patient image clicked on by the user click action.

12. The computer system of claim 11, further comprising: providing one or more recommendations to the user, wherein the one or more recommendations are based on at least one or more similar patients identified in a connected database, wherein the one or more similar patients are identified in the connected database using at least one information retrieval algorithm.

13. The computer system of claim 11, wherein the characteristics comprise at least a size and a location of the medical image positive finding.

14. A non-transitory computer program product for medical report generation, comprising:

one or more non-transitory computer-readable storage media and program instructions stored on at least one of the one or more non-transitory computer-readable storage media, the program instructions executable by a processor to cause the processor to specifically configure the processor to implement a medical report generation computer system, wherein the medical report generation computer system operates to perform a method comprising:

receiving, by the medical report generation computer system, a plurality of patient images of a patient;

executing, in the medical report generation computer system, an imaging machine learning model on the plurality of patient images to output, based on a processing of the plurality of patient images through the imaging machine learning model, a medical image positive finding, wherein the imaging machine learning model is a convolutional neural network (CNN) pretrained based on a database of existing patient medical images;

executing, in the medical report generation computer system, a segmentation CNN model on the plurality of patient images to identify characteristics of the medical image positive finding;

executing, in the medical report generation computer system, a text monitoring machine learning model based on the medical image positive finding and the characteristics of the medical image positive finding, to retrieve relevant data comprising relevant patient data, from a patient medical record of the patient, and a relevant medical guideline corresponding to the medical image positive finding and the characteristics of the medical image positive finding, wherein different relevant medical guidelines and patient data are retrieved for different medical image positive findings and different characteristics of the medical image positive finding;

providing the relevant data to a user, wherein the relevant data provided to the user is in accordance with the relevant medical guideline; and monitoring data input to generate a tailored medical report, wherein the text monitoring machine learning model searches for a previous mention in the patient medical record of a previous finding corresponding to the medical image positive finding, wherein providing the relevant data to the user comprises providing an output that specifies whether the previous finding was acted upon and raises an alert for previously detected conditions that require a follow up, and wherein monitoring data input to generate the tailored medical report comprises:

monitoring a user click action on at least one patient image in the plurality of patient images; and modifying an output of the relevant data to the user based on the user click action to provide relevant information corresponding to a portion of the at least one patient image clicked on by the user click action.

15. The non-transitory computer program product of claim 14, wherein the characteristics comprise at least a size and a location of the medical image positive finding.

* * * * *